(12) United States Patent
Montagnino

(10) Patent No.: US 6,454,723 B1
(45) Date of Patent: Sep. 24, 2002

(54) METABOLIC FITNESS TRAINING APPARATUS

(75) Inventor: James Montagnino, St. Charles, IL (US)

(73) Assignee: Sunbeam Products, Inc., Boca Raton, FL (US)

( * ) Notice: Subject to any disclaimer, the term of this patent is extended or adjusted under 35 U.S.C. 154(b) by 0 days.

(21) Appl. No.: 09/819,867

(22) Filed: Mar. 28, 2001

(51) Int. Cl.[7] .................................................. A61B 5/08
(52) U.S. Cl. ........................................ 600/532; 600/531
(58) Field of Search ................................. 600/532, 531, 600/529, 533, 538

(56) References Cited

U.S. PATENT DOCUMENTS 4,735,777 A * 4/1988 Mitsui et al. ................. 422/70
5,425,374 A * 6/1995 Ueda et al. ................... 422/84

* cited by examiner

*Primary Examiner*—Kevin Shaver
*Assistant Examiner*—Navin Natnithithadha
(74) *Attorney, Agent, or Firm*—Kramer, Levin, Naftalis & Frankel LLP

(57) ABSTRACT

A metabolic fitness training apparatus is provided which measures the concentration of acetone in a trainer's breath while exercising. The metabolic fitness training apparatus include a housing, an acetone sensitive sensor, an optical detection circuit, and a mouthpiece attached to the housing. The sensor contains reagents such as salicylaldehyde or derivatives thereof which react with acetone to change the optical transparency of the sensor. The optical detection circuit may include a LED and a photodetector or a photometric instrument to measure the change in optical transparency of the sensor, and convert that change to acetone concentration. There may also be a display for viewing the acetone concentration.

19 Claims, 5 Drawing Sheets

R=H or CH$_3$ 19 n: a-d=1-4 R=H
20 n: a-b=1-2 R=CH$_3$

R=H or CH$_3$   23 n: b-d=2-4

21 n: b-d=2-4 R=H
22 n: b-b=2-2 R=CH$_3$

METABOLIC FITNESS TRAINING APPARATUS

FIELD OF THE INVENTION

This invention relates to a metabolic fitness training apparatus. Namely, the present invention provides an apparatus for monitoring a person's metabolic rate during exercise.

BACKGROUND INFORMATION

Physical training fitness devices are useful because they assist a person in determining how hard his or her body is working and whether or not he/she wants to exercise harder. These physical training fitness devices measure certain body conditions, such as temperature, heart rate, rate of perspiration, calories burned, breathing rate, weight loss, etc. to help guide one in modifying his or her training efforts.

Currently, a number of physical training fitness methods or devices exist to monitor one's health such as urine monitoring of glucose and ketones, or self-blood glucose monitor (SBGM). These type of devices are impractical for use during exercise.

In addition to being unpleasant, urine monitoring is somewhat inaccurate since substances measured in the urine must first be filtered by the kidney and pass through the bladder prior to being available for analysis.

Furthermore, SBGM requires the exerciser to make a fingertip prick with a lancet to produce a drop of capillary blood, transfer the blood to a reagent strip, precisely time the reaction of the blood with the strip, and read the result using either a visual color chart or a reflectance meter. Each of these steps has the ability to introduce error into the measurement.

Physical training fitness devices which can be used during exercise offer a number of advantages over those that cannot be used during exercise by allowing one to adjust in real time his or her training efforts while exercising. The most commonly used type of physical training fitness devices for personal use include those which measure heart rates. In particular, these heart rate measuring devices comprise a sensor which a person can attach to oneself to measure his/her heart rate during exercise. Since there is a beneficial heart rate range to train in, the exerciser can adjust the strength, duration, etc. of his/her training to get the heart rate into that optimum range while exercising.

However, these heart rate measuring physical training devices do not necessarily offer the best safeguard against overexertion. For example, in order for the body to fuel its efforts during exercise, it must metabolize fat (or sugar if available) to convert them into calories for energy. As the body exerts itself harder, it metabolizes more fat by increasing its metabolic rate. However, there is a maximum rate at which fat can be metabolized ("maximum fat burn rate"). This maximum fat burn rate will be exceeded if a body over-exerts itself during exercise. To fulfill its need for more energy when over-exerting itself, the body increases its metabolic rate in excess of the maximum fat burn rate such that the body will begin to undesirably metabolize muscle tissue. Current physical training devices such as a heart rate device would not be able to detect when the maximum fat burn rate has been exceeded.

SUMMARY OF THE INVENTION

The present invention provides a metabolic fitness training apparatus for measuring acetone concentration in a body's exhaling breath as an indicator of the body's metabolic rate.

In an exemplary embodiment of the present invention, a metabolic fitness training apparatus comprises a housing, an acetone sensitive sensor, an optical detection circuit, and a mouthpiece attached to the housing. The sensor contains reagents such as salicylaldehyde or derivatives thereof which react with acetone to change the optical transparency of the sensor. The optical detection circuit may include a LED and a photodetector or a photometric instrument to measure the change in optical transparency of the sensor, and correlate that change to acetone concentration. There may also be a display to view the acetone concentration.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details. Furthermore, well known features may be omitted or simplified in order not to obscure the present invention.

Unlike urine monitoring or SBGM, the present invention assists one in determining whether to exert more or less effort during exercise by monitoring his or her metabolic rate, which is an important physical fitness indicator not measured by a heart rate physical fitness training device. For purposes of this application, any person who is exercising will be referred to as the "exerciser".

To better assess one's metabolic rate during exercise, the present invention measures the level of acetone present in one's breath during exercise. Acetone appears in the breath as a result of the metabolic breakdown ("catabolism") of acetoacetate in the body. Acetoacetate is a chemical substance which is found in fat and muscle tissue. As the metabolic rate of fat increases due to exercise, the catabolism of acetoacetate in fat increases, leading to an increase in the concentration of acetone in one's breath. Because the concentration of acetoacetate in muscle tissue is much higher than in fat, the catabolism of acetoacetate in muscle tissue (which occurs after the maximum fat burn rate is exceeded due to physical overexertion) leads to an even more dramatic increase of acetone concentration in one's breath. Thus, to prevent injury caused by metabolizing muscle tissue during exercise due to overexertion, the present invention measures and displays the level of acetone in one's breath during exercise so that the trainer can decide in real time to increase or scale back his or her training efforts.

Figure 1:
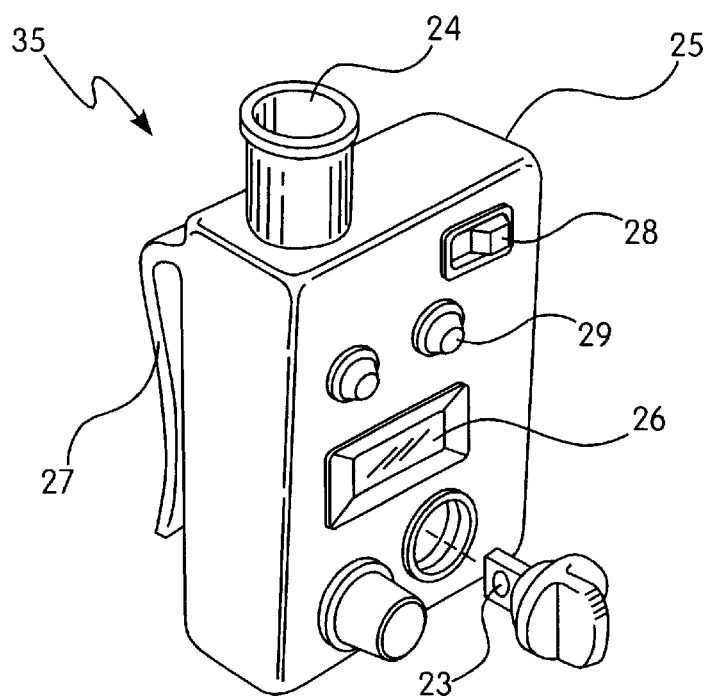
FIG. 1 is an exemplary embodiment of a metabolic fitness training apparatus in accordance with the present invention.
Figure 10:
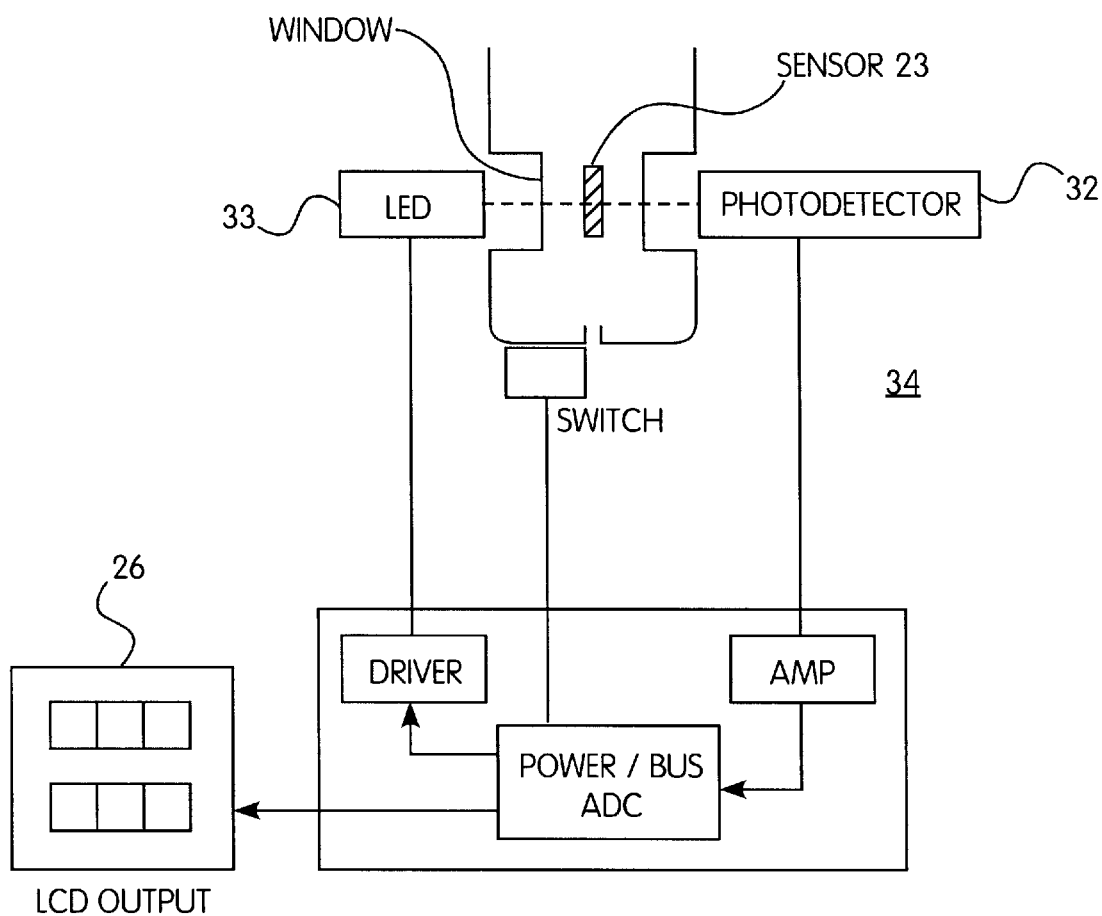
FIG. 10 illustrates a schematic diagram of an exemplary embodiment of a LED/photodetector in accordance with the present invention.

In an exemplary embodiment shown in FIG. 1, an apparatus of the present invention includes a sensor 23, mouthpiece 24, housing 25, and an optical detection circuit 34 (FIG. 10). The optical detection circuit may include a LED 33 and a photodetector 32 or any equivalent photometric instrument for measuring light (FIG. 10). A display 26 may also be present on the housing 25. There is also an optional belt clip 27 attached to the exterior of the housing 25 so that the trainer can conveniently clip the apparatus to his/her waist when exercising and then remove the apparatus to measure his/her breath acetone level at will. The housing 25 may also include a switch 28 and calibration buttons 29.

Figure 2:
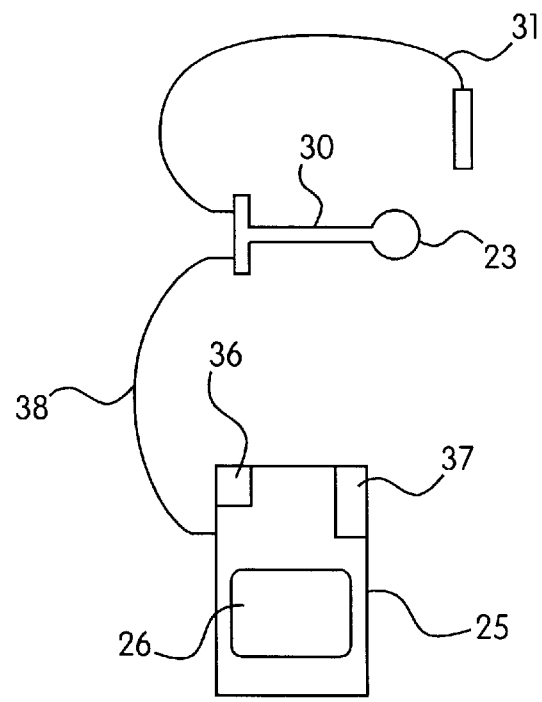
FIG. 2. is an alternative embodiment of a metabolic fitness training apparatus in accordance with the present invention.

In an alternative embodiment as shown in FIG. 2, the apparatus of the present invention includes a sensor 23 attached to a boom 30 of a headset 31. The headset 31 would be worn so that the sensor 23 is positioned at the mouth (not shown) level of the trainer in order to detect breath acetone levels. The boom 30 is further coupled to a housing 25 which may be worn on the trainer's waist or wrist, or attached to a wall.

In an exemplary embodiment of the present invention, the method for measuring breath acetone levels is based on detecting the reaction rate between breath acetone and acetone sensitive materials on sensor 23. The housing 25 contains the optical detection circuit 34 (shown in FIG. 10) which detects the shift in optical transparency of sensor 23 after its exposure to breath acetone.

Figure 3:
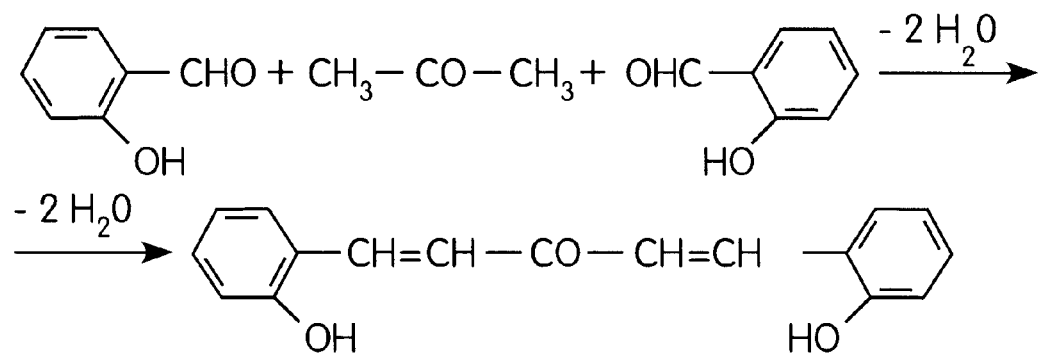
FIG. 3 illustrates a base catalyzed condensation of acetone by two molecules of salicylaldehyde.

In the exemplary embodiment of the present invention, the reaction on sensor 23 involves the base-catalyzed condensation of acetone by two molecules of salicylaldehyde as shown in FIG. 3. The active sensor material is a complex consisting of organic and inorganic compounds which responds to the presence of acetone by changing its color saturation (i.e., from yellow to red). The rate of change in intensity is monitored using an LED 33 and photodiode circuit 34 as shown in FIG. 10. The rate of change in reagent color is related to the concentration of both acetone and of salicylaldehyde or its derivatives.

The reaction of acetone vapor at levels as low as 0.2 ppm has been described in publications such as Feigl, et al., "Spot Tests in Organic Analysis", 455, Elsevier Scientific, New York (1966) in a reaction involving the condensation of salicylaldehyde catalyzed by a base such as NaOH, as shown in FIG. 3. The detection of the reaction of acetone with aldehydes to form a condensed product may be enhanced by modification of the aldehyde to form a monomolecular array.

Figure 4:
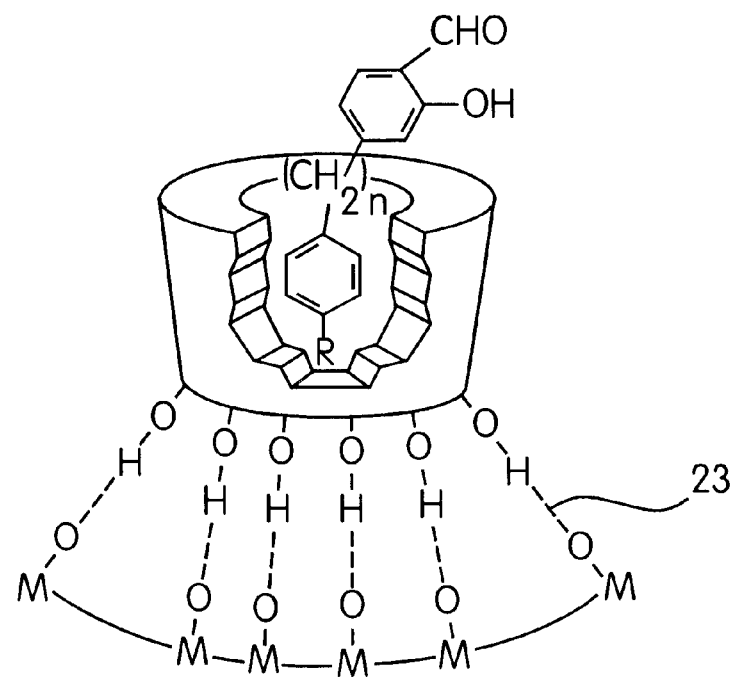
FIG. 4 is a graphical illustration of cyclodextrin on a transparent metal oxide containing a derivative of salicylaldehyde.

Various derivatives of salicylaldehyde can be isolated and stabilized for use with the sensor 23. For example, as shown in FIG. 4, a molecular encapsulant such as cyclodextrin (CD) is formed on the surface of a porous transparent metal oxide of sensor 23, allowing the reagent to be readily encapsulated.

The formation of a host-guest complex with a host such as cyclodextrin (CD) and a salicylaldehyde derivative or similar derivatives, can be made selective for reaction with acetone. In addition, the host provides stability from ultraviolet exposure and oxidation while reducing volatilization loss. The reactions entailed in producing a stable selective acetone sensor are discussed in detail below.

Figure 5:
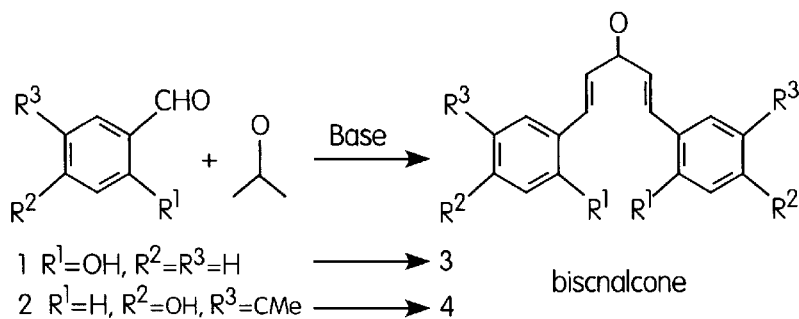
FIG. 5 illustrates condensation reactions by salicylaldehyde and vanillin with acetone to generate a colored bis-chalcone product.
Figure 5:
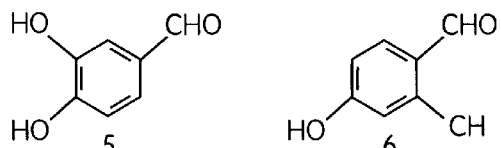

Both salicylaldehyde 1 and vanillin 2 undergo selective condensation reactions with acetone to generate a colored bischalcone product 3, 4 as illustrated in FIG. 5. Vanillin 2 offers a great potential for reagent development through modification of the R group in position 3; this route begins with 3,4-dihydroxybenzaldehyde 5. The compound 2,4-dihydroxybenzaldehyde 6 provides an alternative parent framework from which derivatives can develop; alkylation of 6 occurs at the para hydroxy group and retains the ortho-hydroxybenzaldehyde arrangement found in 1.

Figure 6:
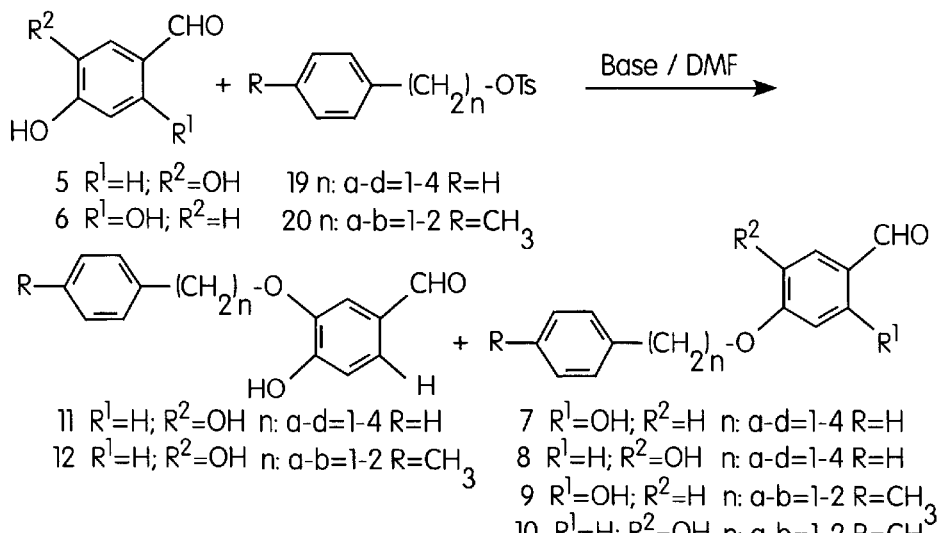
FIG. 6 illustrates the treatment of 3,4 dihydroxybenzaldehyde with phenylalkyltosylate and base to form an ether linkage.
Figure 7:
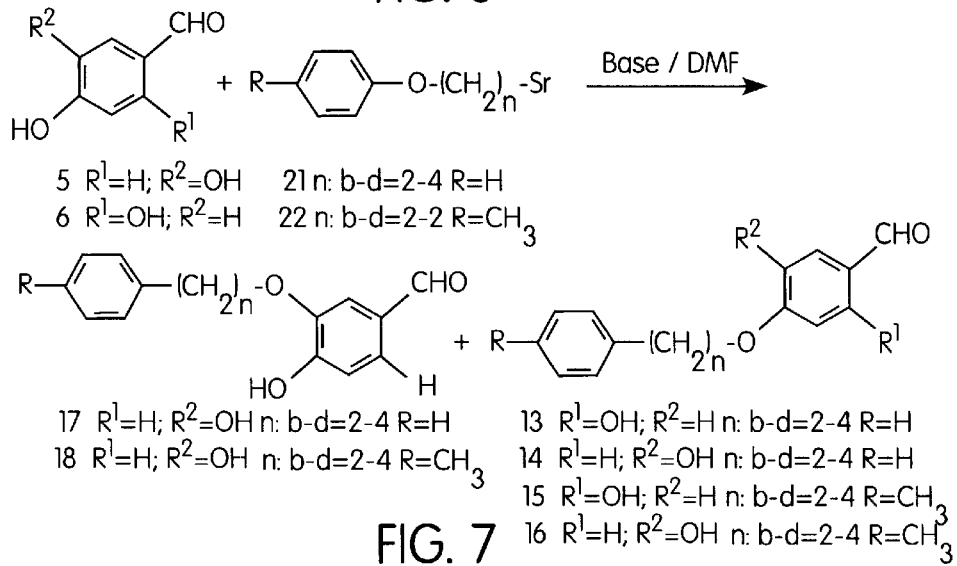
FIG. 7 illustrates the treatment of 3,4-dihydroxybenzaldehyde with phenoxyalkyhalide and base to form an ether linkage.

Anchoring the reagent to the CD-modified surface is of primary import yet at the same time reagent mobility is necessitated by the stoichiometry of the reaction. To better anchor the reagent to the CD, a series of phenylalkyl 7–12 and phenoxyalkyl 13–18, derivatives of 5 and 6 as shown in FIGS. 6 and 7 may be prepared. The additional phenyl group provides a site for anchoring the reagent, the alkyl chain offers mobility of the reactive head group, and the head group ensures the selectivity toward acetone.

Detailed studies on the binding of aromatic units to various CD's have shown that the more hydrophobic the group the better the binding (17, 18, 19 of FIG. 7). Head groups resembling 1 or 2 of FIG. 5 are relatively hydrophilic compared to simple alkyl aromatics. Molecules such as 7–18 of FIGS. 6 and 7 will therefore bind with the simple aromatic in the CD and leave the head group free to react.

Treating derivative 5 with a phenylalkyltosylate 19, 20 (FIG. 6) or phenoxyalkylhalide 21, 22 (FIG. 7) and base forms an ether linkage at either position 3 or 4. Both isomers form in the general reaction, but chromatographic separation of the two products yields pure isomers. Similar conditions with 6 alkylates to form a selective product, thus alleviating the need for chromatographic separation (FIGS. 6 and 7). The notation N: a–d=1–4 in FIG. 8 signifies that four different compounds, identical except for the number of $CH_2$ groups in the tail, will be produced.

Figure 8:
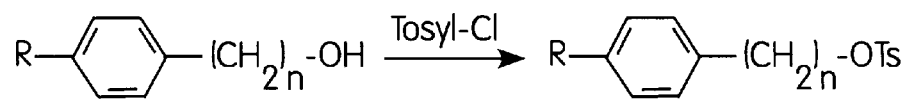
FIG. 8 illustrates the treatment of precursor alcohols of phenylalkyltosylate with tosylchloride to yield tosylates.
Figure 9:
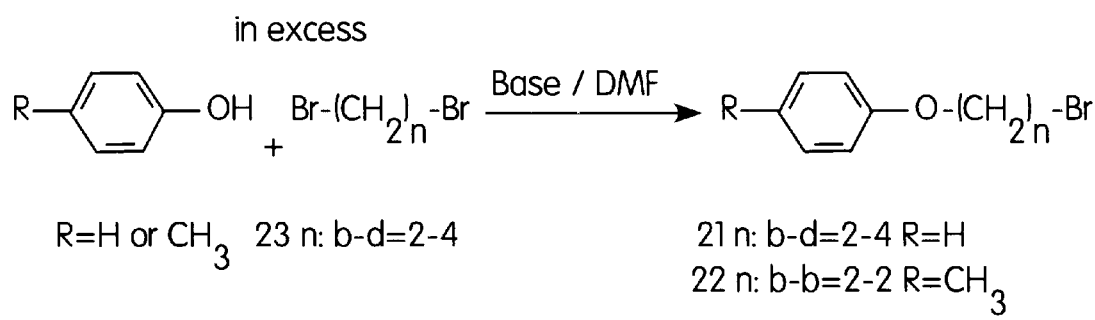
FIG. 9 illustrates the treatment of precursor phenols of phenoxyalkylhalide with base and an excess dihalide to form monohalide.

The reactions 19, 20 of FIG. 8 can be prepared in one step starting from commercially available compounds. The precursor alcohols of 19 and 20 are treated with tosylchloride overnight (or for several hours) to yield the tosylates essentially quantitatively (FIG. 8). The precursor phenols of 21 and 22 are treated with base and an excess of the dihalide of choice 23 to form the monohalide in high yield (FIG. 9).

All of these reactions are synthetic procedures. From these few reactions, there is the potential for a high degree of variability. The value of n can be varied to effect the particular configuration that optimizes the reaction of the salicylaldehyde derivative with acetone, thereby allowing the desired biosensor properties to be tailored as necessary.

Low cost and reliable solid state optical sources and detectors are available for the visible through near IR band (500–1100 nm). Specific chromophoric products of the reaction of salicylaldehyde derivatives with acetone shift the peak absorbance wavelength of the sensor into this spectral region. By Beer's law, the optical absorbance (A) of the chromophore is proportional to its concentration, whose rate of change in turn is proportional to the concentration of acetone and salicylaldehyde derivatives. Therefore, $$dA/dt = K_f[\text{salicylaldehyde derivatives}][\text{acetone}] \quad \text{Eq. 1}$$

with rate constant $K_f$.

The plot of absorbance vs. time in the early stages of the acetone-sensor reaction should be linear, with slope proportional to [acetone], or $$A = K[\text{salicylaldehyde derivatives}][\text{acetone}], \quad \text{Eq. 2}$$

where K is a proportionality constant.

The substrate for the active organic and inorganic compounds involved in the acetone optical darkening mechanism must meet a number of experimental and physical criteria. Its most important physical properties are expected to be pore size, total surface area, physical strength, optical uniformity, and chemical stability in a basic (pH>7) environment. Preferred materials are porous glass manufactured by means of extrusion, heat treatments, and subsequent acid leach and a sol-gel alumina.

The loss of cell sensitivity (i.e., optical absorbance change vs. acetone exposure) may be correlated with the mass loss of sensing materials, indicating that the key mechanism is the loss of volatiles such as water and salicylaldehyde molecules. Thus, proper amounts of molecular encapsulant materials (such as cyclodextrins) may be added to the formulation to enhance moisture and salicylaldehyde retention without degrading the desired response. Cyclodextrins can be attached to the substrate surface through supramolecular forces, and the salicylaldehyde derivative encapsulated as depicted in FIG. 4. The modified sensor disks are expected to be capable of withstanding thermal stressing at 60° C. for more than 60 days, suggesting that a shelf life for the sensor 23 of over five years under normal storage conditions.

As shown in an exemplary embodiment of the present invention at FIG. 10, to measure the concentration of breath acetone, the sensor 23 is placed in the optical path of an LED/photodetector circuit 34. As acetone reacts with the reagents on the sensor 23, the optical transparency of the sensor 23 is decreased and thus, so is the output of the photodetector 32. The rate of change in cell absorbance (A) is then calculated substantially in accordance with Equation 1 and converted to acetone concentration. Thus, the acetone sensitive sensor 23 acts as a dynamic optical filter of the LED output, exhibiting a defined linear relationship between the rate of change in absorbance and its acetone exposure.

Thus, to use an exemplary embodiment of the present invention as illustrated in FIG. 1, the trainer may first turn the switch 28 of the apparatus 35 on. To calibrate the apparatus 35, the trainer may then blow into the mouthpiece 24 of the apparatus 35 while pressing the calibration button 29. The acetone in the breath then reacts with the reagents of sensor 23 to affect the optical transparency of sensor 23. The change in optical transparency is sensed by the photodetector 32 (FIG. 10) and the concentration of acetone is calculated substantially in accordance with Equation 1 as the base acetone concentration.

To measure the breath acetone level during exercise, the trainer would once again blow into the mouthpiece 24 of the apparatus 35. The acetone in the breath then reacts with the reagents of sensor 23 to affect the optical transparency of sensor 23. The change in optical transparency is sensed by the photodetector 32 (FIG. 10) and the concentration of acetone is calculated substantially in accordance with Equation 1.

The acetone concentration can then be displayed on the LCD display 26 as shown in FIG. 1 for the trainer to read.

The LCD display 26 may indicate (i.e., by flashing) when the acetone concentration is close to, has reached, or exceeded the acetone concentration level at the maximum fat burn rate. Other methods of indicating when the acetone concentration is high may be used such as a blinking dot on the LCD display, flashing light, sounding a tune, etc.

To alleviate the slight inconvenience of having to remove the apparatus 35 from the waist each time the trainer wants to measure the acetone level, a trainer could instead use the alternative embodiment as shown in FIG. 2. Here, while the apparatus 35 may still be clipped to the waist or attached to the wrist, the sensor 23 is attached to a boom 30 which is part of a headset 31. The boom 30 would be equipped with a miniature light source and/or photodetector or photometric instrument to measure the change in optical transparency of the sensor 23. The boom 30 would then relay that information by wire 38 to apparatus 35 to determine the acetone concentration. Alternatively, the boom 30 can also relay the information via wireless communication to apparatus 35.

As with FIG. 1, the acetone concentration can then be displayed on the LCD display 26 of FIG. 2 for the trainer to read. Alternatively, apparatus 35 may come equipped with an LED light 36 which will blink or a speaker 37 which will sound an alarm if the acetone level is too high.

One skilled in the art will realize that the method and system of the present invention may be modified as necessary to accommodate anything the operator of the present invention desires, and it is intended to claim all of them as being within the spirit of the present invention.

What is claimed is:

1. A metabolic fitness training apparatus for measuring acetone concentration in a breath comprising:
    a housing;
    an acetone sensitive sensor, said sensor located within said housing;
    an optical detection circuit, said circuit being capable of
        detecting a change in optical transparency of said sensor,
        converting said change in optical transparency to acetone concentration, and
        indicating when said acetone concentration has approximately reached or exceeded an acetone concentration level at a maximum fat burn rate; and
    a mouthpiece attached to said housing.

2. The metabolic fitness training apparatus of claim 1, wherein said sensor further comprises salicylaldehyde or derivatives thereof.

3. The metabolic fitness training apparatus of claim 2, wherein said sensor further comprises cyclodextrin.

4. The metabolic fitness training apparatus of claim 1, wherein the optical detection circuit comprises a LED and a photodetector, and wherein said sensor is positioned in between the LED and the photodetector.

5. The metabolic fitness training apparatus of claim 1, comprising a belt clip.

6. The metabolic fitness training apparatus of claim 1, comprising an LCD display.

7. A metabolic fitness training apparatus for measuring acetone concentration in a breath comprising:
    a headset;
    a boom attached to the headset;
    an acetone sensitive sensor attached to said boom;
    an optical detection circuit, said circuit being capable of
        detecting a change in optical transparency of said sensor,
        converting said change in optical transparency to acetone concentration, and indicating when said acetone concentration has approximately reached or exceeded an acetone concentration level at a maximum fat burn rate; and a housing, said housing being capable of communicating with said boom.

8. The metabolic fitness training apparatus of claim 7, wherein said sensor further comprises salicylaldehyde or derivatives thereof.

9. The metabolic fitness training apparatus of claim 8, wherein said sensor further comprises cyclodextrin.

10. The metabolic fitness training apparatus of claim 7, wherein the optical detection circuit comprises a photometric instrument.

11. The metabolic fitness training apparatus of claim 7, comprising a belt clip.

12. The metabolic fitness training apparatus of claim 7, comprising a LCD display.

13. The metabolic fitness training apparatus of claim 7, comprising an LED indicator.

14. The metabolic fitness training apparatus of claim 7, comprising a speaker.

15. A metabolic fitness training apparatus for measuring acetone concentration in a breath comprising:

an acetone sensitive sensor, said sensor comprising reagents which react with acetone to change the optical transparency of said sensor;

a photometric instrument for detecting a change in optical transparency of said sensor;

a circuit for converting said change in optical transparency of said sensor to an acetone concentration; and a display for viewing the acetone concentration and for indicating when the acetone concentration has approximately reached or exceeded an acetone concentration level at a maximum fat burn rate.

16. The metabolic fitness training apparatus of claim 15, wherein said sensor further comprises salicylaldehyde or derivatives thereof.

17. The metabolic fitness training apparatus of claim 15, wherein said sensor further comprise cyclodextrin.

18. The method of monitoring metabolic rate during exercise comprising the steps of:

reacting an acetone sensitive reagent on a sensor with acetone present in a breath;

detecting a change in optical transparency of the sensor;

converting said change in optical transparency to an acetone concentration;

displaying said acetone concentration; and indicating when said acetone concentration has approximately reached or exceeded an acetone concentration level at a maximum fat burn rate.

19. The method of monitoring metabolic rate during exercise of claim 18, comprising the step of reacting salicylaldehyde or derivatives thereof on a sensor with acetone present in a breath.

* * * * *